United States Patent
Hu

(10) Patent No.: US 10,131,621 B2
(45) Date of Patent: Nov. 20, 2018

(54) PROCESS FOR RECOVERING AMINOALCOHOLS AND GLYCOLS FROM AQUEOUS STREAMS OF TAURINE PRODUCTION

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 8 days.

(21) Appl. No.: 15/366,835

(22) Filed: Dec. 1, 2016

(65) Prior Publication Data

US 2018/0155272 A1  Jun. 7, 2018

(51) Int. Cl.
| | | |
|---|---|---|
| *C07C 209/86* | (2006.01) | |
| *C07C 29/86* | (2006.01) | |
| *C07B 63/00* | (2006.01) | |
| *C02F 1/66* | (2006.01) | |
| *C02F 1/26* | (2006.01) | |
| *B01D 11/04* | (2006.01) | |
| *C07C 41/38* | (2006.01) | |
| *C02F 103/36* | (2006.01) | |

(52) U.S. Cl.
CPC ........ *C07C 209/86* (2013.01); *B01D 11/0492* (2013.01); *C02F 1/26* (2013.01); *C02F 1/66* (2013.01); *C07B 63/00* (2013.01); *C07C 29/86* (2013.01); *C07C 41/38* (2013.01); *C02F 2103/36* (2013.01)

(58) Field of Classification Search
None
See application file for complete search history.

(56) References Cited

U.S. PATENT DOCUMENTS

| | | |
|---|---|---|
| 5,646,320 A | 6/1997 | Cassady et al. |
| 5,739,365 A | 4/1998 | Briody et al. |
| 5,763,632 A | 6/1998 | Cassady et al. |
| 8,609,890 B1 | 12/2013 | Hu |
| 9,061,976 B1 | 6/2015 | Hu |
| 9,145,359 B2 | 9/2015 | Hu |
| 9,428,450 B2 | 8/2016 | Hu |
| 9,428,451 B2 | 8/2016 | Hu |

*Primary Examiner* — Clinton A Brooks
*Assistant Examiner* — Jennifer C Sawyer
(74) *Attorney, Agent, or Firm* — Myers, Wolin, LLC

(57) ABSTRACT

There is disclosed an extraction process for recovering aminoalcohols and glycols from aqueous streams of taurine production. The aqueous streams which contain aminoalcohols and/or glycols are first mixed with a base to increase pH and then extracted with $C_3$-$C_6$ alcohols, ketones, and ethers. The aqueous streams are then returned to their respective cyclic process for the production of taurine.

8 Claims, No Drawings

PROCESS FOR RECOVERING AMINOALCOHOLS AND GLYCOLS FROM AQUEOUS STREAMS OF TAURINE PRODUCTION

TECHNICAL FIELD

This invention relates to a process for recovering aminoalcohols and glycols from aqueous streams of taurine production.

BACKGROUND OF THE INVENTION

Taurine can be referred to as 2-aminoethylsulfonic acid and is of the formula $H_2NCH_2CH_2SO_3H$. Taurine is an extremely useful compound because it per se has such pharmacological effects as detoxification effect, fatigue-relieving effect and nourishing and tonifying effect. As a result, taurine finds wide applications as an essential ingredient for human and animal nutrition.

Many chemical synthetic methods have been known in the prior arts for the preparation of taurine and related derivatives. The following two methods have been used in industry to manufacture over 60,000 tons of taurine per year, starting from ethylene oxide (the EO process) or monoethanolamine (the MEA process).

According to the EO process disclosed in U.S. Pat. Nos. U.S. Pat. No. 8,609,890, U.S. Pat. No. 9,061,976, U.S. Pat. No. 9,428,450 and U.S. Pat. No. 9,428,451, ethylene oxide is reacted with sodium bisulfite to obtain sodium isethionate, which undergoes ammonolysis reaction to yield sodium taurinate. Neutralization with an acid results in a mixture of taurine and inorganic salt. During the reaction of ethylene oxide with aqueous sodium bisulfite, significant amount of ethylene glycol and diethylene glycol is formed as byproducts. After ammonolysis reaction of the crude sodium isethionate, ethanolamine is also formed in the process. After the separation of taurine and inorganic salt, typically sodium sulfate, current industrial process leaves behind a large amount of waste stream containing glycols, monoethanolamine, sodium taurinates, and sodium isethionate.

Copending U.S. Ser. No. 15/268,071 discloses a novel variation of the EO process for producing taurine from ammonium isethionate, which is prepared from the reaction of ethylene oxide with aqueous ammonium bisulfate. According to U.S. Pat. Nos. 5,646,320, U.S. Pat. No. 5,739,365, and U.S. Pat. No. 5,763,632, the reaction of ethylene oxide with ammonium bisulfite produces some ethylene glycol and monoethanolamine as byproducts even under best controlled reaction conditions. After concentration and crystallization of ammonium isethionate, the mother liquor is enriched with monoethanolamine as isethionate salt and ethylene glycol, which make further isolation of ammonium isethionate difficult. When the crude ammonium isethionate is used in the cyclic process for producing taurine, accumulation of monoethanolamine and ethylene glycol in the process renders a large purge of mother liquor necessary.

According to the MEA process disclosed in U.S. Pat. No. 9,145,359, monoethanolamine is reacted first with sulfuric acid to afford 2-aminoethyl hydrogen sulfonate ester, which undergoes sulfonation reaction with ammonium sulfite to yield a mixture of taurine and ammonium sulfate. During the sulfonation reaction, up to 15% of the intermediate ester is hydrolyzed to monoethanolamine, which is left in the waste stream as its sulfate salt, along with ammonium sulfite and ammonium sulfate, or along with sodium sulfite and sodium sulfate when sodium sulfite is used as sulfonation agent.

It is the principal object of the present invention to disclose an extraction process for recovering aminoalcohols and glycols from aqueous streams of taurine production from ethylene oxide or monoethanolamine. According to the process disclosed in the present invention, the aqueous streams, after removing of aminoalcohols and glycols, can be returned to the cyclic process for the production of taurine.

DESCRIPTION OF THE INVENTION

This invention is related to a liquid-liquid extraction process for recovering aminoalcohols and glycols from the aqueous streams of taurine production from ethylene oxide or monoethanolamine. More specifically, it is focused on removing monoethanolamine and ethylene glycol from the cyclic process of producing taurine using ethylene oxide or monoethanolamine as starting materials. The removal of these impurities greatly reduces the amount of purge solution from a cyclic process and increases the overall yield of taurine as the aqueous streams are returned to the production process.

The extraction process according to the present invention starts with adjusting the pH of the aqueous stream with a base to basic, preferably to 10-12, if the starting aqueous solution is neutral and contains aminoalcohols.

The base used to adjust the pH of the aqueous solutions is selected from the group comprised of ammonium hydroxide, alkali hydroxides, and alkali carbonates. The cation of the base is preferably the same as the one inherently present in the aqueous solution, but different cations can be utilized with the same effect. For example, in an aqueous solution of ammonium isethionate or ammonium sulfate, ammonia or ammonium hydroxide is preferably used. For the aqueous solution of alkali taurinate, particularly sodium taurinates, or sodium isethionate, sodium hydroxide is preferably applied. The alkali metals are lithium, sodium, potassium, and cesium.

After the pH adjustment to basic, the solution is mixed and vigorously agitated with an organic solvent to form a thoroughly mixed phase. After settling, the two phases are separated into an organic phase and an aqueous phase. The organic phase is distilled to recover the organic solvent for reuse, and the recovered aminoalcohols and glycols can be further separated and purified by distillation according to methods known in prior art. The recovered aminoalcohols and glycols can be sold as byproducts, used for other applications, or recycled into the production of taurine in the case of monoethanolamine.

After the removal of aminoalcohols and glycols, the aqueous phase is stripped of the residual solvent by distillation or by methods known in prior art. The aqueous stream is then returned to the production stage of the process.

For aqueous streams containing both aminoalcohols and glycols, a two-stage extraction process can be used. In the first stage, the aqueous stream is extracted directly with an organic solvent without adjusting the pH, so that glycols can be selectively removed. In the second stage, the aqueous phase is mixed with a base to a basic pH, then extracted again to remove aminoalcohols and glycols.

For aqueous streams containing only glycols, no pH adjustment is necessary, as glycols can he extracted from a solution of acid, neutral, and basic pH.

Effective extraction solvents are found from the group of organic solvents comprised of $C_3$-$C_6$ alcohols, ketones, and ethers. More particularly, the organic extractant is selected from n-propanol, isopropanol, n-butanol, 2-butanol, isobutanol, tert-butanol, acetone, butanone, pentanone, methyl isobutyl ketone, cyclohexanone, diethylether, and methyl tert-butyl ether. Preferably, the extraction solvent is n-propanol and isopropanol, and most preferably isopropanol. A single solvent or a mixture of two or more solvents can be used in the extraction process.

The extraction process according to the present invention can be carried out discontinuously, semi-continuously, or continuously.

EXAMPLES

The following examples will illustrate the practice of this invention but are not intended to limit its scope.

Example 1

This example relates to the simultaneous recovery of monoethanolamine and ethylene glycol from crystallization mother liquor of ammonium isethionate.

To 100 g of the crystallization mother liquor of ammonium isethionate, containing 64% ammonium isethionate, 4.5% monoethanolamine, and 4.2% ethylene glycol, was added 10 mL of 24% ammonium hydroxide. The solution was extracted three times each with 35 mL of isopropanol containing 5% ammonium hydroxide.

After the extraction, the aqueous phase contained 1.8% monoethanolamine and 1.6% ethylene glycol.

Example 2

This example relates to the two stage recovery of monoethanolamine and ethylene glycol from crystallization mother liquor of ammonium isethionate.

100 g of the crystallization mother liquor of ammonium isethionate at a pH of 6.7, containing 64% ammonium isethionate, 4.5% monoethanolamine, and 4.2% ethylene glycol, was extracted three times each with 35 mL of isopropanol containing 5% water. The ethylene glycol content was reduced to 1.8% and monoethanolamine content remained the same.

To the extracted solution was then added 5 mL, of 25% ammonium hydroxide. The solution was extracted three times each with 35 mL of isopropanol containing 5% ammonium hydroxide. After the extraction, the aqueous phase contained 1.9% monoethanolamine and 0.8% ethylene glycol.

Example 3

This example relates to the recovery of monoethanolamine and ethylene glycol from crystallization mother liquor of taurine by the EO process.

To 100 g of the crystallization mother liquor of taurine, containing 18% sodium sulfate, 15% sodium ditaurinate, 1.5% sodium tritaurinate, and 4% taurine, 4.5% ethylene glycol, and 0.8% monoethanolamine, was added 4 mL of 30% sodium hydroxide. The solution was extracted three times each with 35 mL, of isopropanol. The temperature was maintained at 40° C. during the extraction and phase separation to prevent the precipitation of sodium sulfate. The content of ethylene glycol was lowered from 4.5% to 2.7%, and the monoethanolamine from 0.8% to 0.3%.

Example 4

This example relates to the recovery of monoethanolamine and ethylene glycol from crystallization mother liquor of taurine by the EO process according to U.S. Ser. No 15/268,071.

To 100 g of the crystallization mother liquor of taurine, containing 45% sodium isethionate, 12% sodium ditaurinate, 1.5% sodium tritaurinate, and 4% taurine, 5.4% ethylene glycol, and 3.6% monoethanolamine, was added 4 mL of 30% sodium hydroxide. The solution was extracted three times each with 35 mL of isopropanol. The content of ethylene glycol was lowered from 5.4% to 2.3%, and the monoethanolamine from 3.6% to 1.4%.

Example 5

This example relates to the recovery of monoethanolamine from crystallization mother liquor of taurine by the MEA process according to U.S. Pat. No. 9,145,359.

To 100 g of the crystallization mother liquor of taurine, containing 46% ammonium sulfate, 14% ammonium sulfite, 25% monoethanolamine as sulfate salt, was added 20 mL of 24% ammonium hydroxide. The solution was then extracted three times each with 50 mL of isopropanol containing 5% ammonium hydroxide. The content of monoethanolamine was lowered to 6.5%.

Example 6

This example relates to the recovery of monoethanolamine from crystallization mother liquor of taurine by the MEA process using sodium sulfite as sulfonating agent.

To 100 g of the crystallization mother liquor of taurine, containing 24% sodium sulfate, 4% sodium sulfite, 12% monoethanolamine as sulfate salt, was added 10 mL of 30% sodium hydroxide. The solution was then extracted three times each with 50 mL of isopropanol containing 5% sodium hydroxide. The content of monoethanolamine was lowered to 2.6%.

It will be understood that the foregoing examples and explanation are for illustrative purposes only and that various modifications of the present invention will be self-evident to those skilled in the art. Such modifications are to be included within the spirit and purview of this application and the scope of the appended claims.

What is claimed is:

1. A process for recovering monoethanolamine and/or ethylene glycols from an aqueous stream of taurine production from ethylene oxide or monoethanolamine, comprising:
   (a) adjusting the pH of an aqueous stream from taurine production from less than 8 to a pH up to 12 to recover monoethanolamine;
   (b) adding isopropanol to an aqueous stream of taurine production and agitating to form a mixed phase;
   (c) separating the mixed phase into an isopropanol phase and an aqueous phase; and
   (d) recovering isopropanol to obtain monoethanolamine and/or ethylene glycols.

2. The process according to claim 1, wherein the pH of an aqueous stream is adjusted to 10 to 12 for the extraction of monoethanolamine with a base selected from the group consisting of ammonium hydroxide, lithium hydroxide, sodium hydroxide, potassium hydroxide, lithium carbonate, sodium carbonate, potassium carbonate, and a mixture of two or more thereof.

3. The process according to claim 1, wherein the aqueous stream is the crystallization mother liquor of ammonium isethionate from the addition reaction of ethylene oxide and ammonium bisulfite.

4. The process according to claim 1, wherein the aqueous stream is the crystallization mother liquor of taurine containing sodium isethionate, sodium ditaurinate, and sodium trituarinate in a cyclic process for producing taurine from isethionic acid or ammonium isethionate.

5. The process according to claim 1, wherein the aqueous stream is the crystallization mother liquor of taurine containing sodium sulfite and/or sodium bisulfite in the production of taurine from ethylene oxide and by using sulfur dioxide as an acid for neutralization.

6. The process according to claim 1, wherein the aqueous stream is the crystallization mother liquor of taurine containing sodium sulfate and sodium taurinates in the production of taurine from ethylene oxide and by using sulfuric acid as an acid for neutralization.

7. The process according to claim 1, wherein the aqueous stream is the crystallization mother liquor of taurine containing ammonium sulfate and ammonium sulfite in the production of taurine from monoethanolamine and by using ammonium sulfite as a sulfonating agent.

8. The process according to claim 1, wherein the aqueous stream is the crystallization mother liquor of taurine containing sodium sulfate and sodium sulfite in the production of taurine from monoethanolamine and by using sodium sulfite as a sulfonating agent.

* * * * *